United States Patent [19]
Weerasooriya et al.

[11] Patent Number: 6,147,246
[45] Date of Patent: Nov. 14, 2000

[54] PROCESS FOR PREPARING ALKOXYLATED DIALKYL CARBONATE COMPOUNDS

[75] Inventors: Upali Weerasooriya; K. Lee Matheson; Dewey L. Smith, all of Austin; Paul A. Filler, Leander; Elida G. Partain, Cedar Park; Kelly D. Knouse, Round Rock; Janet L. Watson, Leander, all of Tex.

[73] Assignee: Condea Vista Company, Houston, Tex.

[21] Appl. No.: 09/471,967

[22] Filed: Dec. 23, 1999

[51] Int. Cl.[7] ........................................ C07C 68/06
[52] U.S. Cl. .......................... 558/276; 558/275; 516/204
[58] Field of Search ...................................... 558/275, 276

[56] References Cited

U.S. PATENT DOCUMENTS

| | | |
|---|---|---|
| 2,503,280 | 4/1950 | Lockwood . |
| 2,507,088 | 5/1950 | Bradley . |
| 3,260,744 | 7/1966 | Ito et al. . |
| 3,320,174 | 5/1967 | Rubinfeld . |
| 3,372,188 | 3/1968 | Alston et al. . |
| 4,504,418 | 3/1985 | Langdon . |
| 4,754,075 | 6/1988 | Knopf et al. . |
| 4,775,653 | 10/1988 | Leach et al. . |
| 4,820,673 | 4/1989 | Knopf et al. . |
| 4,835,321 | 5/1989 | Leach et al. . |
| 5,104,487 | 4/1992 | Taggart et al. . |
| 5,191,104 | 3/1993 | King . |
| 5,220,046 | 6/1993 | Leach et al. . |
| 5,386,045 | 1/1995 | Weerasooriya et al. . |
| 5,627,121 | 5/1997 | Lin et al. . |
| 5,773,860 | 3/1998 | Durbut et al. . |

OTHER PUBLICATIONS

C. Ovalles, R. L. Marquez, R. Curci, L. Prat, E. Lujano, and J. Portillo: Synthesis, Characterization, and Surface Activity of Surfactants Derived from Nonylphenol, Ethylene Oxide and Carbon Dioxide. J. Dispersion Science and Technology, 17(4), 1996, pp. 353–366.

C. Ovalles, R. L. Marquez, E. Lujano, W. Aular, R. Curci, and J. Portillo: Surface Activity and Emulsification Properties of Surfactants Derived from Nonlyphenol Ethoxylated, Ethylene Oxide and Carbon Dioxide. J. Dispersion Science and Technology, 18(1), 1997, pp. 1–9.

*Primary Examiner*—Michael G. Ambrose
*Attorney, Agent, or Firm*—Browning Bushman

[57] ABSTRACT

A process for alkoxylating an organic carbonate wherein an alkylene oxide is reacted with an organic carbonate such as a dialkyl carbonate in the presence of a catalytically effective amount of a calcium-containing catalyst to produce alkoxylated carbonates.

9 Claims, No Drawings

PROCESS FOR PREPARING ALKOXYLATED DIALKYL CARBONATE COMPOUNDS

BACKGROUND OF THE INVENTION

1. Field of the Invention

The present invention relates to a process for the alkoxylation of a carboxylated compound and, more specifically, to a process for producing alkoxylated dialkyl carbonates.

2. Description of the Prior Art

It is known that certain calcium-containing compounds can be used to form catalysts to alkoxylate a wide variety of compounds such as alcohols and carboxylated compounds. Example of calcium-containing catalysts for carrying out such alkoxylation reactions are shown, for example, in U.S. Pat. Nos. 4,754,075; 4,820,673; 4,835,321; 5,220,046; 5,386,045; and 5,627,121, all of which are incorporated herein by reference. Additionally, the alkoxylation of carboxylated compounds using mixed metal oxide catalysts or a modified bimetallic or polymetallic catalyst are disclosed in U.S. Pat. Nos. 5,191,104 and 5,104,487, both of which are incorporated herein by reference.

SUMMARY OF THE INVENTION

It is an object of the present invention to provide a process for the alkoxylation of carboxylated compounds.

It is another object of the present invention to provide a process for alkoxylating dialkyl carbonates.

The above and other objects of the present invention will become apparent from the description given herein and the claims.

In accordance with the present invention, there is provided a process for alkoxylating a carboxylated compound comprising reacting an alkylene oxide containing from 2 to 4 carbon atoms with an organic carbonate having the formula:

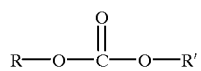

(I)

wherein R and R' can be the same or different and are a hydrocarbyl group having from 1 to 30 carbon atoms, said reaction being conducted at a temperature of from about 80° C. to about 200° C. and in the presence of a catalytically effective amount of a catalyst selected from the group consisting of (1) Calcium Catalyst A formed by reacting a reactant mixture comprising an alkoxylated alcohol mixture containing compounds having the general formula:

$$R_1-O-(C_mH_{2m}O)_pH \quad (II)$$

wherein $R_1$ is an organic radical containing from about 1 to about 30 carbon atoms, m is 2 to 4, and p is from 1 to 50, a calcium-containing compound which is at least partially dispersible in said alkoxylated alcohol mixture, an organic and/or an inorganic acid compound, and a metal alkoxide of a Lewis acidic metal, said calcium-containing compound and said alkoxylated alcohol mixture being mixed prior to addition of said metal alkoxide, said reactant mixture being heated to a temperature and for a time sufficient to effect at least a partial exchange reaction between the alkoxide groups of said metal alkoxide and said hydroxyl groups of said alkoxylated alcohol, (2) Calcium Catalyst B formed by solubilizing, at least partially, a calcium-containing compound with an activator having the formula:

$$Z_a-X-Q-Y-Z'_b \quad (III)$$

wherein X and Y are the same or different electronegative heteroatoms selected from the group consisting of oxygen, nitrogen, sulfur, and phosphorus, a and b are the same or different integers satisfying the valency requirements of X and Y, Q is an organic radical that is electropositive or essentially neutral relative as to X and/or Y, and Z and Z' are the same or different and are either hydrogen or an organic radical that does not prevent said solubilizing (3) Calcium Catalyst C formed by admixing an alkoxylated alcohol mixture containing compounds having the general formula II, a calcium-containing compound that is at least partially dispersible in said alkoxylated alcohol mixture, and a carboxylic acid having from about 4 to about 15 carbon atoms, the mole ratio of calcium to said carboxylic acid being from about 15:1 to 1:1, to produce a calcium-containing composition having titratable alkalinity, said calcium-containing composition optionally being obtained under conditions to prevent loss of water, and adding an amount of an inorganic acid to neutralize at least 25% of said titratable alkalinity, optionally under conditions to prevent loss of water, and (4) mixtures of Calcium Catalyst A, Calcium Catalyst B, and Calcium Catalyst C.

DESCRIPTION OF THE PREFERRED EMBODIMENTS

The organic carboxylates that can be alkoxylated according to the present invention are those having the formula:

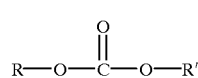

(I)

wherein R and R' can be the same or different and are a hydrocarbyl group having from 1 to 30 carbon atoms. Although the hydrocarbyl group will preferably be an alkyl group containing from 6 to 20 carbon atoms, it can be the residue of any organic compound. Thus, in a broad aspect, the hydrocarbyl group includes acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, and the like. Specific, nonlimiting examples of organic carboxylates that can be alkoxylated in accordance with the process of the present invention include dihexyl carbonate, didecyl carbonate, ditetradecyl carbonate, wherein R and R' are the organic residue(s) of Guerbert alcohols, linear alcohols, etc.

The alkoxylated carboxylated compounds that can be made in accordance with the process of the present invention include compounds having the following formulae:

(IV)

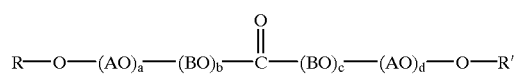

(V)

and mixtures thereof, wherein R and R' are hydrocarbyl groups described above, n is from 2 to 4, x and y are independently from 1 to 30, AO and BO are independently an

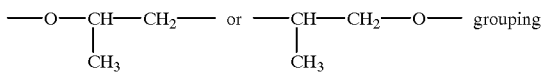

or a—$CH_2$—$CH_2$—O— grouping, provided that when one of AO or BO is a

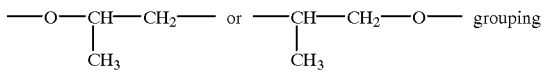

the other of AO or BO is an

and a, b, c, and d are independently from 1 to 20.

According to the process of the present invention, an organic carbonate as described above is reacted with an alkylene oxide containing from 2 to 4 carbon atoms. Thus, alkylene oxides, such as ethylene oxide, propylene oxide, butylene oxide, trimethylene oxide, etc., can be used. It will be understood that mixtures of such alkylene oxides, e.g., mixtures of ethylene oxide and propylene oxide, can be employed. Thus, it will be appreciated that the alkoxylated carboxylates can contain an oxyalkylene chain that is heteric in nature (when a single alkylene oxide is employed), block in nature (when two or more alkylene oxides are employed), or random in nature (when two or more alkylene oxides are employed). In general, the amount of alkylene oxide used will be such as to provide an alkylene oxide content of from about 10 to about 90% by weight of the alkoxylated carbonate. It will be appreciated that the amount of the alkylene oxide employed can be varied over wide limits to tailor the end products for desired purposes. For example, in certain applications, it may be more desirable that the average number of alkoxy groups per molecule be of relatively low number, e.g., from about 2 to about 8, whereas in other applications it may be desirable that the number of alkoxy groups be greater, e.g., from about 8 to about 30.

The catalysts that can be used in the process of the present invention are calcium-based catalysts—i.e., derived from calcium compounds. The three types of calcium catalysts that can be used in the process of the present invention, referred to as Calcium Catalyst A, Calcium Catalyst B, and Calcium Catalyst C can be prepared by methods well known in the art. Thus, Calcium Catalyst A can be produced by the method disclosed in U.S. Pat. No. 4,775,653, incorporated herein by reference for all purposes, Calcium Catalyst B can be prepared by the method disclosed in U.S. Pat. No. 4,820,673, incorporated herein by reference for all purposes, and Calcium Catalyst C can be prepared by the method disclosed in U.S. Pat. No. 5,627,121, incorporated herein by reference for all purposes.

The calcium compound used in making the catalysts may include a compound such as calcium hydride, calcium acetate, calcium oxylate, calcium nitrate, etc. However, it is preferred that the calcium compound be calcium oxide, calcium hydroxide, or a mixture thereof.

The alkoxylated organic carbonates of the present invention, as noted, can be prepared by reacting a suitable organic carbonate starting material, a suitable alkylene oxide (s) in the presence of a catalytically effective amount of Catalyst A, Catalyst B, Catalyst C, or mixture thereof. In the case of Calcium Catalysts A and C, the amount of catalyst employed will generally be from about 0.1 to about 20% based upon the total reaction mixture. For example, if the weight of the reaction mixture, including all the alkylene oxide, is 300 g, typically from about 0.3 g to about 60 g of Calcium Catalyst A or C would be employed in the reaction. In the case of Calcium Catalyst B, and since Calcium Catalyst B is a less efficient catalytic species, the amount of Calcium Catalyst B employed will generally range from about 3 to about 90% of the total reaction mixture.

The process of the present invention can be conducted over a wide range of temperature and pressure conditions. For example, the reactions can be conducted at temperatures ranging from about 80° C. or lower to about 200° C. and higher. Pressures can range from subambient up to about 100 psi, pressures of from about 10 to about 60 psi being preferred.

Since the method of preparing Calcium Catalyst A is clearly taught in U. S. Pat. No. 4,775,653, it need not be discussed in detail herein. However, in general, Calcium Catalyst A is prepared by forming a catalyst premix by admixing and reacting an alkoxylated alcohol mixture containing an alkoxylated alcohol having the general formula:

wherein $R_1$ is an organic radical containing from about 1 to about 30 carbon atoms, m is 2 to 4, and p is 1 to 50, a calcium-containing compound that is at least partially dispersible in the alkoxylated alcohol mixture, an organic and/or an inorganic acid compound, and a metal alkoxide of a Lewis acidic metal such as aluminum titanium, vanadium, etc. Especially preferred are metal alkoxides selected from compounds having the formula:

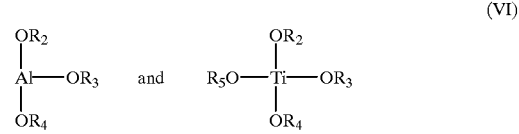

wherein $R_2$, $R_3$, $R_4$, and $R_5$ are each a hydrocarbon radical containing from about 1 to about 30, preferably from about 8 to about 14, carbon atoms, the calcium-containing compound and the alkoxylated alcohol mixture being mixed prior to addition of the metal alkoxide and heating the catalyst premix to a temperature and for a time sufficient to effect at least a partial exchange reaction between the alkoxide groups of the metal alkoxide and the hydroxyl groups of the alkoxylated alcohol. While the use of titanium alkoxides is not disclosed in U.S. Pat. No. 4,775,653, in preparing Calcium Catalyst A, the titanium alkoxide is merely substituted for the aluminum alkoxide or, if desired, a mixture of the aluminum alkoxide and titanium alkoxide can be employed.

In a similar vein, since the preparation of Calcium Catalyst B is clearly taught in U.S. Pat. No. 4,820,673, it is unnecessary to provide a detailed description of its preparation herein. However, in general, Calcium Catalyst B is formed by solubilizing, at least partially, a calcium-containing compound with an activator having the formula:

wherein X and Y are the same or different electronegative heteroatoms selected from the group consisting of oxygen, nitrogen, sulfur, and phosphorus, a and b are the same or different integers satisfying the valency requirements of X and Y, Q is an organic radical that is electropositive or essentially neutral relative as to X and/or Y, and Z and Z' are the same or different and are either hydrogen or an organic radical that does not prevent said solubilizing.

The preparation of Calcium Catalyst C is set out in U.S Pat. No. 5,627,121. Calcium Catalyst C is formed by admixing an alkoxylated alcohol mixture containing alkoxylated alcohols having the formula II above with a calcium-containing compound that is at least partially dispersible in the alkoxylated alcohol mixture, and a carboxylic acid having from about 4 to about 15 carbon atoms, the mol ratio of calcium to the carboxylic acid being from about 15:1 to 1:1, to produce a calcium-containing compound having titratable alkalinity. Preferably, the calcium-containing compound is obtained under conditions that prevent loss of water. An inorganic acid is then added to the calcium-containing composition to neutralize at least 25% of the titratable alkalinity, again preferably under conditions to prevent loss of water. This results in a partially neutralized calcium-containing catalyst suitable for the alkoxylation reaction of the present invention.

It will be appreciated that mixtures of any or all of Calcium Catalysts A, B, or C can be employed as well.

Generally, the alkoxylation reaction of the present invention can be conducted by charging a suitable reaction vessel with the dialkyl carbonate, the reactor being heated, e.g., by placing in a heating block or the like, so that a temperature of from about 100 to about 175° C. can be achieved. Typically, the mixture is heated to the desired temperature under nitrogen or some suitable inert gas. The reactor is then placed under a nitrogen sparge to remove water, if present. The catalyst is then injected into the reaction mixture and the temperature raised to the desired reaction temperature, the reaction mixture being maintained under a nitrogen blanket. When the desired reaction temperature is achieved, the reactor is evacuated and the chosen alkylene oxide introduced at the appropriate pressure. As the alkylene oxide reacts, additional amounts are added, the temperature being maintained substantially constant throughout the reaction.

The alkoxylated dialkyl carbonates produced by the process of the present invention can be used in surfactant applications, i.e., in combination with other surfactants such as linear alkyl benzene sulfonates, alcohol sulfates, etc. Additionally, the alkoxylated carbonates can be tailored to produce lubricants, low melting functional fluids—i.c., heat exchange fluids—etc.

In order to illustrate the invention, the following non-limiting examples are presented.

EXPERIMENTAL PROCEDURE

The alkoxylation catalyst used was a Calcium Catalyst A. Alkoxylations with both ethylene oxide and propylene oxide were performed as follows: 300 g of a selected dialkyl carbonate was charged to a stainless steel autoclave equipped with a magnetic stir bar, an internal cooling line, and thermocouples. The autoclave was placed in a heating block controlled using an $I_2R$ Therm-O-Watch TCP3-1200 controller. The cooling line in the autoclave was hooked up to either water or air for cooling. The cooling lines were controlled using a Therm-O-Watch Model L9- 1500 RTD controller. A cooling line was opened or closed, depending on temperature readings from the autoclave thermocouple. A 500 ml bomb containing the alkylene oxide under 50 lbs. (23kg) of $N_2$ pressure was connected in parallel with a graduated sight glass and connected to the autoclave via stainless steel tubing. The mixture in the autoclave was heated under nitrogen at 100° C., at which time a vacuum is applied to produce a nitrogen sparge of 5 psig in the reactor. The reaction mixture is sufficiently dry after 20 minutes of sparging. Calcium Catalyst A in an amount of 0.8% by weight (based on the final weight of the ethoxylated dialkyl carbonate) was then introduced into the autoclave. The temperature was subsequently raised to 175° C., with nitrogen blanketing the reaction mixture. At 175° C., the Nitrogen flow is cut-off and the alkylene oxide introduced at a pressure of approximately 50 psig. Subsequent amounts of the alkylene oxide are introduced into the reactor when the pressure drops as a result of ethoxylation. Temperature is maintained at or near 175° C. throughout the reaction. If desired, phosphoric acid can be added to the reaction mixture in an amount of 0.08 g of 85% phosphoric acid per gram of catalyst used to destroy the catalyst. Further, if desired, the reaction product can be filtered to remove catalyst particles. Using the above procedure, the following alkoxylated dialkyl carbonates were prepared:

Dihexyl Carbonate. Ethoxylated dihexyl carbonates containing 65, 75, and 85% by weight ethylene oxide, respectively, were prepared.

Didecyl Carbonate. Ethoxylated didecyl carbonates containing 65, 75, 80, and 85% by weight ethylene oxide, respectively, were prepared.

Ditetradecyl Carbonate. Ethoxylated ditetradecyl carbonates containing 65, 75, and 85% by weight ethylene oxide, respectively, were prepared.

$C_{16}$ Guerbet Residue Carbonates. Propoxylated carbonate wherein R and R' were the residues of a $C_{16}$ Guerbet alcohol was prepared. The di-propoxylated carbonate contained 6 and 14 moles of propylene oxide. In a separate reaction, the same carbonate was reacted with 5 moles of ethylene oxide to prepare the ethoxylated carbonate.

$C_{12}$ Guerbet Residue Carbonates. An ethoxylated carbonate wherein R and R' were the residue of a $C_{12}$ Guerbet alcohol was prepared. The ethoxylated carbonate contained 5 moles of ethylene oxide.

In all cases, NMR analysis of the reaction products described above confirm that alkoxylation occurred between the carbonyl carbon and both of the R—O— and R'—O— groups.

As noted, the alkoxylated organic carbonates prepared by the method of the present invention can be mixed with anionic surfactants to formulate cleaning compositions for a wide variety of uses.

The anionic surfactants that can be mixed with the alkoxylated dialkyl carbonates prepared by the process of the present invention can generally be any conventionally used water-soluble anionic surfactant or mixtures thereof. As used herein, the term "anionic surfactant" is intended to refer to the class of anionic and mixed anionic-nonionic surfactants providing detersive action.

Suitable water-soluble non-soap, anionic detergents include those surface-active compounds that contain an organic hydrophobic group containing generally 8 to 26 carbon atoms, preferably 10 to 18 carbon atoms, in their molecular structure and at least one water-solubilizing group selected from the group of sulfonates, sulfates, and carboxylates so as to form a water-soluble surfactant. Usually, the hydrophobic group will include or comprise a $C_8$–$C_{22}$, alkyl, aralkyl, or acyl group. Such surfactants are generally employed in the form of water-soluble salts having a salt-forming cation usually selected from the group consisting of sodium, potassium, ammonium, magnesium, and mono-, di-, or tri-$C_2$–$C_3$ alkanolammonium, with sodium, potassium, and ammonium cations being preferred.

Non-limiting examples of suitable sulfonated anionic surfactants include aralkyl mononuclear aromatic sulfonates such as higher alkylbenzene sulfonates containing from 10 to 16 carbon atoms, $C_8$–$C_{15}$ alkyl toluene sulfonates, and $C_8$–$C_{15}$ alkyl phenol sulfonates, wherein the alkyl group in the aforementioned sulfonates can be in a straight or branched chain. A preferred sulfonate is a linear alkylbenzene sulfonate having a high content of 3- (or higher) phenyl isomers and a correspondingly low content (well below 50%) of 2- (or lower) phenyl isomers—i.e., wherein the benzene ring is preferably attached in large part at the 3 or higher (for example, 4, 5, 6, or 7) position of the alkyl group and the content of the isomers in which the benzene ring is attached in the 2 or 1 positions correspondingly low. Particularly preferred materials are set forth in U.S. Pat. No. 3,320,174, incorporated herein by reference for all purposes.

Other suitable anionic surfactants are the olefin sulfonates, including long-chain alkene sulfonates, long-chain hydroxy alkane sulfonates, or mixtures of alkene sulfonates and hydroxy alkane sulfonates. These olefin sulfonates and their method of preparation are well known to those skilled in the art. Preferred olefin sulfonates contain from 14 to 16 carbon atoms and are obtained by sulfonating an alpha-olefin or an internal olefin.

Other examples of suitable anionic sulfonate surfactants are the paraffin sulfonates containing 10 to 20, preferably 13 to 17, carbon atoms. Primary paraffin sulfonates are made by reacting long-chain alpha-olefins and bisulfites and paraffin sulfonates (SAS) having the sulfonate group distributed along the paraffin chain, as shown in U.S. Pat. Nos. 2,503,280; 2,507,088; 3,260,744; and 3,372,188 and German Patent No. 735096, all of which are incorporated herein by reference for all purposes.

Useful anionic sulfate surfactants are the $C_8$–$C_{18}$ alkyl sulfate salts and the $C_8$–$C_{18}$ alkyl ether polyethenoxy sulfate salts having the formula:

$$R(OC_2H_4)_nOSO_3M \tag{VI}$$

wherein n is 1 to 12, preferably 1 to 5, and M is a solubilizing cation selected from the group consisting of sodium, potassium, ammonium, magnesium, and mono-, di- and triethanol ammonium ions. Methods of preparing the alkyl sulfates and the alkyl ether polyethenoxy sulfates are well known to those skilled in the art. Preferred alkyl sulfates and alkyl ether polyethenoxy sulfates contain 10 to 16 carbon atoms in the alkyl group.

It will be apparent to those skilled in the art that the sulfate, anionic surfactants can be present either in salt form, depending upon the pH of the final composition, with the salt-forming cations being the same as described above.

Of the anionic surfactants noted above, the preferred surfactants are the $C_9$–$C_{15}$ linear alkylbenzene sulfonates, the $C_{13}$–$C_{17}$ paraffin or alkane sulfonates, and the $C_8$–$C_{18}$ alkyl sulfates.

Generally speaking, the anionic surfactant will be present in the compositions of the present invention in an amount of from about 10 to about 90% by weight, preferably from 50 to 90% by weight, based on the combined weight of the anionic surfactant and the alkoxylated carbonate.

The compositions of the present invention can also include nonionic surfactants such as primary aliphatic alcohol ethoxylates, secondary aliphatic alcohol ethoxylates, alkyl phenol ethoxylates, and ethylene oxide-propylene oxide condensates of primary alcohols.

When formulated into cleaning preparations such as hard surface cleaning agents, the compositions of the present invention, in addition to water, can also include, as disclosed in International Publication No. WO98/00418, incorporated herein by reference for all purposes, compounds such as co-surfactants, hard water additives such as magnesium salts, foam suppressants, dyes, bacteriacides, preservatives or antioxidants, pH-adjusting agents, opacifiers, perfumes, solubilizing agents, sequestering agents, pearlescing agents, alkyl polysaccharide surfactants, and other adjuvants as long as they do not adversely affect the detersive properties of the composition. The amounts of such additional additives in formulating cleaning agents in accordance with the composition of the present invention can be easily determined depending upon the specific type of cleaning agent desired, and those skilled in the art are readily able to select the amount and type of adjuvant to be added to the compositions of the present invention in formulating end-use cleaning compositions, e.g., hard surface cleaning agents. Additionally, the propoxylated dialkyl carbonates exhibit excellent low temperature properties, making them ideally suited as lubricants.

The foregoing description and examples illustrate selected embodiments of the present invention. In light thereof, variations and modifications will be suggested to one skilled in the art, all of which are in the spirit and purview of this invention.

What is claimed is:

1. A process for the alkoxylation of a dialkyl carbonate comprising reacting an alkylene oxide containing from 2 to 4 carbon atoms, with a dialkyl carbonate having the formula:

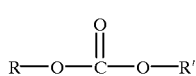

$$\tag{I}$$

wherein R and R' can be the same or different and are a hydrocarbyl group having from 1 to 30 carbon atoms, said reaction being conducted at a temperature of from about 80° C. to about 200° C. and in the presence of a catalytically effective amount of a catalyst selected from the group consisting of (1) Calcium Catalyst A formed by reacting a reactant mixture comprising an alkoxylated alcohol mixture containing compounds having the general formula:

$$R_1—O—(C_mH_{2m}O)_pH \tag{II}$$

wherein $R_1$ is an organic radical containing from about 1 to about 30 carbon atoms, m is 2 to 4, and p is from 1 to 50, a calcium-containing compound which is at least partially dispersible in said alkoxylated alcohol mixture, an organic and/or an inorganic acid compound, and a metal alkoxide of a Lewis acidic metal, said calcium-containing compound and said alkoxylated alcohol mixture being mixed prior to addition of said metal alkoxide, said reactant mixture being heated to a temperature and for a time sufficient to effect at least a partial exchange reaction between the alkoxide groups of said metal alkoxide and said hydroxyl groups of said alkoxylated alcohol, (2) Calcium Catalyst B formed by solubilizing, at least partially, a calcium-containing compound with an activator having the formula:

$$Z_a—X—Q—Y—Z'_b \tag{III}$$

wherein X and Y are the same or different electronegative heteroatoms selected from the group consisting of oxygen, nitrogen, sulfur, and phosphorus, a and b are the same or different integers satisfying the valency requirements of X and Y, Q is an organic radical that is electropositive or essentially neutral relative as to X and/or Y, and Z and Z' are the same or different and are either hydrogen or an organic radical that does not prevent said solubilizing (3) Calcium Catalyst C formed by admixing an alkoxylated alcohol mixture containing compounds having the general formula II, a calcium-containing compound that is at least partially dispersible in said alkoxylated alcohol mixture, and a carboxylic acid having from about 4 to about 15 carbon atoms, the mole ratio of calcium to said carboxylic acid being from about 15:1 to 1:1, to produce a calcium-containing composition having titratable alkalinity, said calcium-containing composition being obtained under conditions to prevent loss of water, and adding an amount of an inorganic acid to neutralize at least 25% of said titratable alkalinity under conditions to prevent loss of water, and (4) mixtures of Calcium Catalyst A, Calcium Catalyst B, and Calcium Catalyst C.

2. The process of claim 1 wherein said calcium-containing compound is selected from the group consisting of calcium oxide, calcium hydroxide, and mixtures thereof.

3. The process of claim 1 wherein R and $R_1$ can be the same or different and are a hydrocarbyl group containing from 1 to 30 carbon atoms.

4. The process of claim 3 wherein said hydrocarbyl group is an alkyl group containing from 1 to 20 carbon atoms.

5. The process of claim 1 wherein the catalyst is Calcium Catalyst A.

6. The process of claim 1 wherein said inorganic acid compound comprises an inorganic acid.

7. The process of claim 6 wherein said inorganic acid comprises sulfuric acid.

8. The process of claim 5 wherein said inorganic acid compound comprises an acid salt.

9. The process of claim 1 wherein said catalyst comprises Calcium Catalyst C.

\* \* \* \* \*